US00PP09489P

United States Patent [19]

Endisch et al.

[11] Patent Number: Plant 9,489

[45] Date of Patent: Mar. 26, 1996

[54] GERANIUM PLANT NAMED FARO

[75] Inventors: Gerd Endisch, Geranienweg, D-76767 Hagenbach; Ursula Endisch-Burmeister, Bad Kreuznach, both of Germany; Wolf Endisch, Valle Guerra/Teneriffa, Spain

[73] Assignee: Gerd Endisch, Hagenbach, Germany

[21] Appl. No.: 384,010

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,940 4/1987 Schumann ..... Plt./87.12

P.P. 7,609 7/1991 Winner ..... Plt./87.12

P.P. 8,192 3/1993 Holden ..... Plt./87.12

P.P. 8,727 5/1994 Schumann ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Faro' is characterized by a signal red flower color, a semi-double flower forum, dark foliage, medium height, large umbel, long pedicel, medium flower response and good heat and rain resistance.

1 Drawing Sheet

BACKGROUND OF THE NEW PLANT

The present invention comprises a new and distinct cultivar of geranium botanically known as *Pelargonium zonale*, and hereinafter referred to by the cultivar name 'Faro'.

'Faro' is a product of planned breeding program which had the objective of creating new geranium cultivars with signal red flower color, semi-double flower form, dark medium habit.

Faro originated from a hybridization made in a controlled breeding program in Hagenbach, Germany, in 1990. The female parent was 'Komet', characterized by its red, semi-double flower, dark foliage, late flower response and tall habit. The male parent of 'Faro' was 'Bruni', characterized by its red flower colors, semi-double flower form, medium green foliage, compact habit, medium zonation of the leaves, Both 'Komet' and 'Bruni' were patented in Germany but neither is presently available commerically. Its dark foliage distinguishes 'Faro' from 'Bruni'. Its compact habit distinguishes Faro from 'Komet'.

'Faro' was discovered and selected as one flowering plant within the progeny of the stated cross by the inventors in August 1991 in a controlled Environment in Hagenbach, Germany.

DESCRIPTION OF THE NEW PLANT

The first act of asexual reproduction of 'Faro' was accomplished when vegetative cuttings were taken from the initial selection in January 1992 in a controlled Environment in Hagenbach, Germany, by a technician working under formulations established and supervised by Gerd Endisch.

Horticultural examination of selected units initiated in May 1992 has demonstrated that the combination of characteristics as herein disclosed for 'Faro' are firmly fixed and are tetained through successive generations of asexual reproduction.

'Faro' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. The dimensions and measurements given below are approximate.

The following traits have been repeatedly observed and are determined to be basic characteristics of 'Faro' to distinguish this geranium as a new and distinct cultivar:

1. signal red flower color
2. semi-double flower form
3. dark foliage
4. medium height
5. large umbel
6. long pedicel
7. medium flower response
8. good heat and rain resistance.

Of the many commercial cultivars known to the present inventors, the most similar in comparison to 'Faro' is 'Tango'. Reference is made to Chart A below which compares certain characteristics of 'Faro' to those same characteristics of Tango. In comparison to 'Tango', 'Faro' has a broader width, bigger umbel, longer pedicel, shorter peduncle and later flower response.

BRIEF DESCRIPTION OF THE DRAWING

The accompanying photographic drawing show typical flower and foliage characteristics of 'Faro', with colors being as true as possible with illustrations of this type.

DETAILED BOTANICAL DESCRIPTION

In the following description color references are made to The *Royal Horticultural Society Colour Chart* (R.H.S.). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zonal geranium cv. 'Faro'.

Inflorescence:

*Umbel.*—Comprises approx. 38 flowers.

Average diameter.—Approx. 116 mm.

*Average depth.*—Approx. 70 mm.

*Peduncle length.*—Approx. 145–150 mm.

*Spring flowering response period.*—In Hannover (Bundessortenamt) first flower Apr. 21, 1994; 50% of plants with at least one flower opened 13 weeks after planting of unrooted cuttings.

*Outdoor flower production.*—The flower count in 1993 indicated between 65–70 flowers per plant for May 15 through Aug. 15 observation period.

*Durability.*—Good rain resistance. Good heat resistance.

Corolla:

*Blooming habit.*—Continuous, until frost destroys plant.

*Average diameter.*—Approx. 42–45 mm.

*Form.*—Semi-double; cup shaped when bloom first opens, flattening to shallow cup with maturity.

*Petals.*—Normally 7–8.

*Color.*—(General tonality from a distance of three meters) signal red.

*Color of upper petals.*—R.H.S. 43 A (top surface); R.H.S. 43 B (bottom surface).

*Color of lower petals.*—R.H.S. 43 B (top surface); R.H.S. 43 C (bottom surface).

*Pedicel length.*—Approx. 35–38 mm.

*Pedicel color.*—Red (anthocyanin colored).

*Petaloids.*—Normally 2–5 of varying size, colored as petals.

*Persistence.*—Non-shattering flower.

BUD:

*Size.*—Approx. 1.5–2.0 cm across.

*Shape.*—Initially ovate.

*Color.*—Green with anthocyanin at the base.

*Sepals.*—Five in number; pointed linear lanceolate; at time of petal appearance about 12 mm in lenght.

Reproductive organs:

Stamens.— Anthers: 6–7. Filaments: Length approx. 4–6 mm; white. Pollen: Orange.

*Pistal.*— No.: 1. Length: Approx. 9 mmm. Stigma: 5 lobes; color red. Style: Approx. 3 mm in length, color red.

*Ovaries.*—Green.

Fruit.—Partially fertile.

Plant:

*Foliage.*—Abundant quantity, leaves with slight zonation. Size: Approx. 7–8 cm across. Shape: Slightly upwardly cupped, reniform. Margin: Bicrenate. Texture: Leathery. Ribs & Veins: distinct venation on the bottom side, but not prominent on the top surface. Color (upper surface): Dark green, R.H.S. 137 A/B. Color (zonation): Slightly green. Color (bottom surface): R.H.S. 137 C.

*General appearance and from.*—Bushy. Internode length: Approx. 28–29 mm. Branching pattern: Very good self-branching branching characteristic, 18 branches observed Aug. 15, 1994. Height: Approx. 19–21 cm from media surface.

CHART A

| | New Cultivar Name: 'Faro' | Comparison Cultivar Name: 'Tango' |
|---|---|---|
| Umbel diameter | 116 | 100 mm |
| depth | 70 | 48–50 mm |
| Penduncle length | 145–150 | 155–160 mm |
| Pedicle length | 35–38 | 30–32 mm |
| Internode length | 28–29 | 26–27 mm |
| Flower response (first flower) | April 21, 1994 | August 8, 1994 |

What is claimed is:

1. A new and distinct cultivar of Geranium plant known as 'Faro', as described and illustrated and particularly characterized by a signal red flower color, a semi-double flower forum, dark foliage, medium height, large umbel, long pedicel, medium flower response and good heat and rain resistance.

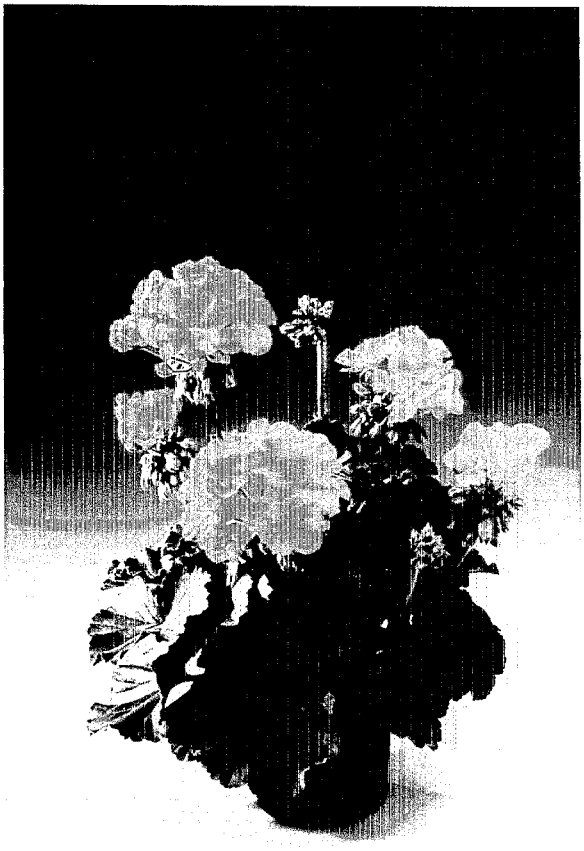

* * * * *